United States Patent [19]

Machin

[11] Plant 4,346

[45] Dec. 12, 1978

[54] CHRYSANTHEMUM PLANT

[75] Inventor: Barrie J. Machin, Littlehampton, England

[73] Assignee: Framptons Nurseries Limited, Chichester, England

[21] Appl. No.: 806,012

[22] Filed: Jun. 13, 1977

[51] Int. Cl.[2] ..... A01H 5/00

[52] U.S. Cl. ..... Plt./80

[58] Field of Search ..... Plt./76, 80

*Primary Examiner*—Robert E. Bagwill

*Attorney, Agent, or Firm*—Brisebois & Kruger

[57] ABSTRACT

A new variety of *Chrysanthemum morifolium* Bailey of the pink open terminal spray type, characterized by the combination of improved color, especially during high light and temperature periods, a strong uniform spray, a longer growing season, and flowers less prone to bruising and damping than the pink open spray type chrysanthemums.

1 Drawing Figure

1

This invention relates to a new and distinct variety of *Chrysanthemum morifolium* Bailey (spray type) known as "Pink Gin".

My new variety was originated by me from a cross made in 1972 between a seedling which originated from a cross between two seedlings of unknown parentage which were produced in the course of a previous cross breeding program and the variety "Rosechip", the former being the seed parent and the latter being the pollen parent.

This new variety resulted from an extensive breeding program with the objective of producing an open terminal spray type with a dependable color under a wide range of controlled year-round growing conditions. "Pink Gin" fulfills the need for a new pink spray, especially during high light and temperature periods, as "Bluechip" and "Rosechip", the most similar sprays grown in Britain, lose their color.

The following unique combination of characteristics distinguishes "Pink Gin" over its parents, and over the variety "Bluechip", as well as all other varieties of which I am aware:

1. Improved color especially during high light and temperature periods.

2. A stronger and more uniform spray produced throughout resulting in a higher percentage grade of market flowers.

3. A longer growing season than "Bluechip" and "Rosechip".

4. Although the flowers are slightly softer than "Bluechip" and "Rosechip" they are less prone to bruising and damping.

Asexual production of this new variety as performed in Sussex, England, by rooting vegetative shoots shows that the above characteristics are fixed and come true to type through succeeding generations.

The accompanying drawing shows a typical flower of my new variety depicted in color as nearly true as it is reasonably possible to make the same in a color illustration of this type.

The following is a detailed description of the new variety "Pink Gin" with color terminology in accor-

2 dance with the Royal Horticultural Society color chart, (R.H.S.).

Genus: Chrysanthemum.
Species: *morifolium* Bailey.
Type: Spray.
Class: Incurving decorative.
Breeding: A cross between an unnamed seedling and "Rosechip", the former being the seed parent and the latter being the pollen parent.
Propagation: Holds its distinguising characteristics through succeeding propagations by rooting vegetative shoots.
Bloom:
*Size.*—Average diameter 7 cms. Average depth 2.5 cms.
*Petalage.*—220–240 Ray petals, 1–10 Disc petals.
*Color of open bloom.*—Inner face of fully expanded petal R.H.S. 73D. Outer face of fully expanded petal R.H.S. 73B.
Response group: 10 weeks.
Temperature tolerance: 56°–60° F at night.
Plant: Strong upright habit of growth.
Foliage: Good quality with average internode length, thick, leathery medium size and medium texture margin deeply cut, tips of lobes pointed, sinus rounded, color R.H.S. 147A.
Stem: Medium thickness and strong.
Water uptake: Good.

I claim:

1. A new and distinct variety of *Chrysanthemum* morifolium Bailey of the pink open terminal spray type, substantially as herein shown and described, characterized particularly as to novelty by the unique combination of improved color, especially during high light and temperature periods, a strong uniform spray, a longer growing season, and flowers less prone to bruising and damping than the pink open spray type chrysanthemums heretofore known.

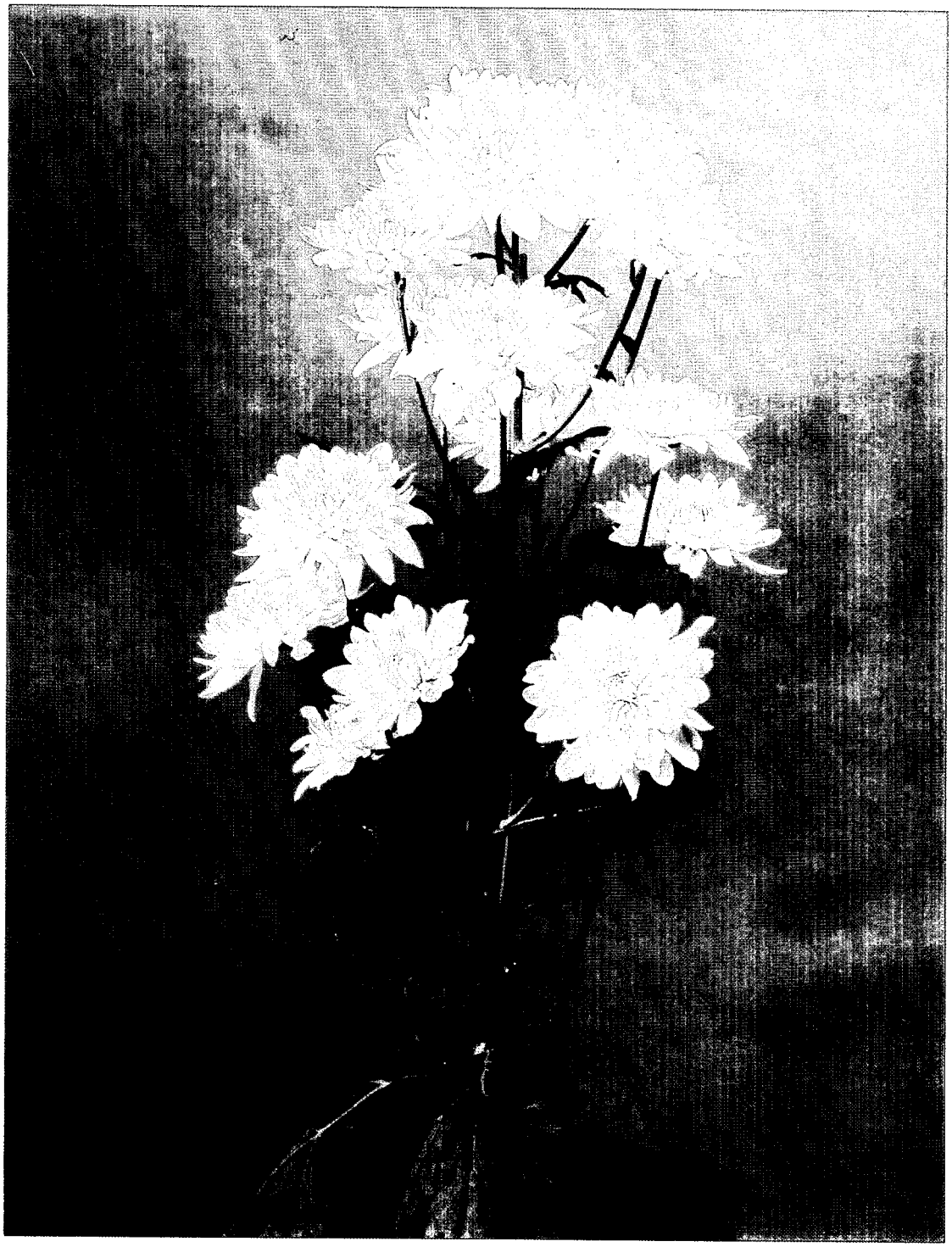

* * * * *